United States Patent
Zhuravkov (12)

(10) Patent No.: US 6,545,480 B1
(45) Date of Patent: Apr. 8, 2003

(54) METHOD FOR CARRYING OUT THE ELECTRICAL BREAKDOWN OF A GASEOUS DIELECTRIC IN A HIGHLY NON-UNIFORM FIELD

(75) Inventor: Igor Viktorovich Zhuravkov, Moscow (RU)

(73) Assignee: Valery Venginovich Starikov, Novokuznetsk (RU); part interest ( * ) Notice: Subject to any disclaimer, the term of this patent is extended or adjusted under 35 U.S.C. 154(b) by 0 days.

(21) Appl. No.: 09/600,560

(22) PCT Filed: Jun. 19, 1998

(86) PCT No.: PCT/RU98/00179

§ 371 (c)(1),
(2), (4) Date: Jul. 19, 2000

(87) PCT Pub. No.: WO98/48268

PCT Pub. Date: Oct. 29, 1998

(30) Foreign Application Priority Data

Feb. 10, 1998 (RU) .............................. 98102523

(51) Int. Cl.$^7$ ................................ G01R 29/12
(52) U.S. Cl. ................ 324/457; 324/459; 324/537; 324/464
(58) Field of Search .................... 324/122, 419, 324/475, 537, 464, 72.5, 109, 357, 457, 459, 452, 754, 758, 761; 361/230, 120, 126, 235; 364/579

(56) References Cited

U.S. PATENT DOCUMENTS 3,639,831 A * 2/1972 Cushman
3,801,899 A * 4/1974 Liao
4,245,187 A * 1/1981 Wagner
4,742,427 A * 5/1988 Richman

FOREIGN PATENT DOCUMENTS

| EP | 0 458 505 A1 | 5/1991 |
| FR | 2109455 | 10/1970 |
| SU | 590588 | 10/1976 |
| SU | 913494 | 7/1980 |
| SU | 1665855 A1 | 8/1989 |

* cited by examiner

Primary Examiner—Michael Sherry
Assistant Examiner—Trung Nguyen
(74) Attorney, Agent, or Firm—Lackenbach Siegel LLP

(57) ABSTRACT

The invention pertains to testing technique and designed to be used in the research n the dielectric rigidity of high-voltage equipment gaseous isolation. The technical result of the invention is the achievement of gas dielectric breakdown with relatively low voltage. A corona discharge is generated by supplying the initial voltage to the electrodes, defining the discharge gap so as to ensure a three dimensional load at the corona-producing electrode. Then, the total voltage, sufficient for complete breakdown, is supplied to the discharge gap with the uniformly distributed three-dimensional load and the breakdown of a gaseous dielectric takes place. The present method provides the decrease of corona discharge and formation of impulse pedestal with the help of additional dynamic discharger in the circuit, which electrodes are switched from the closed state to the open one.

3 Claims, 1 Drawing Sheet

METHOD FOR CARRYING OUT THE ELECTRICAL BREAKDOWN OF A GASEOUS DIELECTRIC IN A HIGHLY NON-UNIFORM FIELD

BACKGROUND OF THE INVENTION

1. Field of the Invention

This invention relates to testing techniques and is designed to be used, for example, in researching the dielectric strength of high-voltage equipment in an environment of gaseous insulation.

2. Description of the Prior Art

Any construction of this kind of testing equipment must consider the necessity of making a higher voltage power supply unit with considerably higher power. This causes some difficulties in manufacturing, and results in unsatisfactory weight and dimensions for such equipment.

In implementing various technical solutions to the problem herein, attempts have been made to perform the gaseous dielectric breakdown with a power supply unit of relatively low voltage. Among those methods that provide the above-mentioned effect are found (1) a technical solution that provides for the injection of hot gases into a discharge gap (SU, 232358, H01 H, Nov. 12, 1968); (2) a technical solution that provides for the injection of gaseous bubbles of cavitation origin (SU, 1072166, H01 T 1/20, Feb. 7, 1984); and a technical solution that provides for covering one of the electrodes with an activating layer (DE, 3621254, H01 T 1/20, Jan. 7, 1988).

All the known methods, however, based as they are only on the redistribution of a space charge within a discharge gap, are ineffective and do not allow a considerable decrease of the power supply voltage.

The closest method to the one proposed in the subject invention is the method of performing the electrical breakdown of a gaseous dielectric in a highly non-uniform field. In accordance with this method the initial voltage, which provides a self-maintained discharge, is first supplied to the electrodes defining the discharge gap, and then a voltage pulse base is generated as additional electromotive force is induced in the leads. It finally results in the complete breakdown of the dielectric (SU, 913494, H01 T 3/00, Mar. 15, 1982).

One major shortcoming of the prior art, with its emphasis only on increasing the testing voltage with the help of a voltage pulse base, is its complete inability to cause any considerable decrease in the power supply unit output voltage.

SUMMARY OF THE INVENTION

One object of the present invention is to provide the ability to carry out the electrical breakdown of a gaseous dielectric using a power supply unit with a reduced voltage caused by the application of both methods discussed above, at the same time—using both the preliminary redistribution of a space charge and the further generation of a voltage pulse base in the supply circuit. This permits gaseous insulation and its diagnosis using a power supply unit with a relatively low output voltage.

In accordance with the subject method of the invention, the initial voltage, a voltage sufficient for producing a self-maintained discharge, is first supplied to electrodes that define the discharge gap. The voltage pulse base is then supplied to provide, together with the initial voltage, the complete breakdown of the dielectric. A corona discharge is generated by supplying the initial voltage to the electrodes defining the discharge gap so as to ensure a space charge at the corona-producing electrode. Before the voltage pulse base is generated, the space charge load is uniformly redistributed along the discharge gap by lowering the corona discharge current. Simultaneously, the decrease of the corona discharge current and the formation of the voltage pulse base occurs through the use of a dynamic discharge device, which is integrated to the supply circuit and has its electrodes switched from a closed state into an open one before being bridged by the electrical arc.

BRIEF DESCRIPTION OF THE DRAWING

The drawing shows the electric circuit of the device implementing the proposed method.

DETAILED DESCRIPTION OF THE EMBODIMENTS

Figure 1:
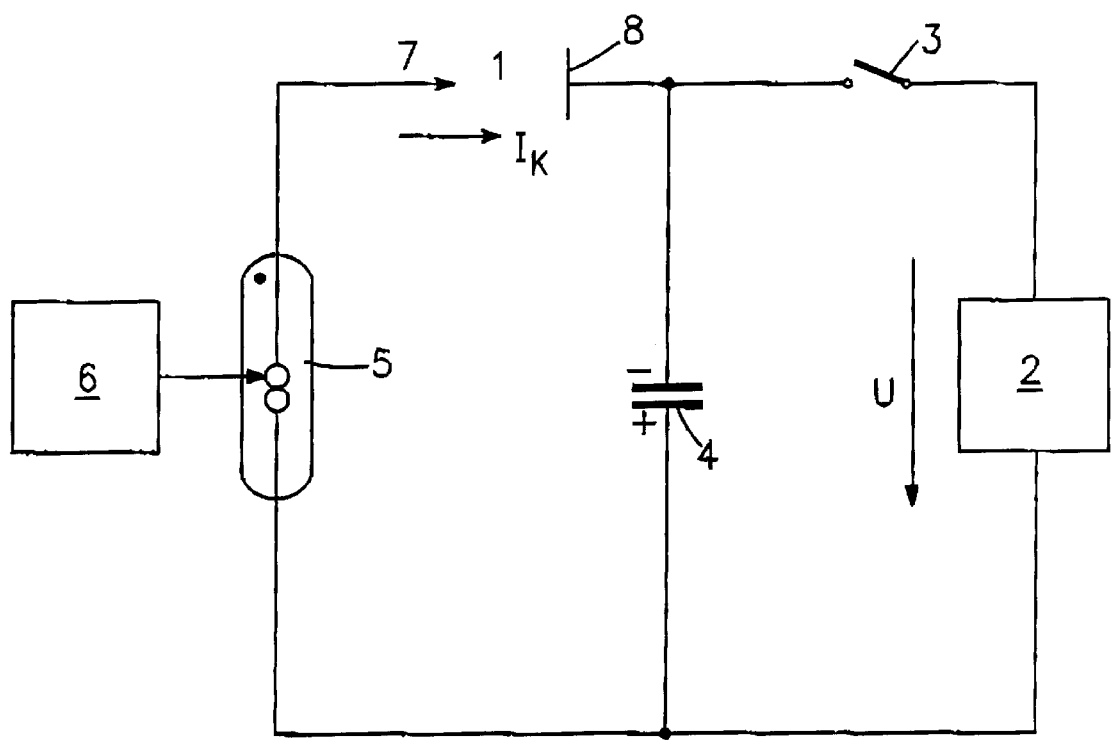

The device includes discharge gap 1 formed by a pin-shaped electrode 7 and a flat electrode 8, power supply unit 2, switch 3, capacitor 4 connected in parallel with the series-connected power supply unit 2, switch 4 and dynamic discharger 5, including an actuator in the form of a pusher 6 with an electromagnet actuating means. Electrodes of the dynamic discharger are embodied in the form of brass spheres, each with of 4 cm. Capacitor 4, discharge gap 1 and dynamic discharger 5, connected in series, form a closed circuit. Gaseous dielectrics to be tested, for example, can be the nitrogen or air filling the discharge gap 1.

The electrical breakdown is caused in the following way:

After turning on switch 3, initial voltage U from the power supply 2, is applied to capacitor 4 and consequently to the discharge gap through the dynamic discharger 5, which has its electrodes coupled together in a closed condition. As a result, between the electrode 7 and the electrode 8 an extremely non-uniform electric field is formed. The initial voltage produces a self-maintained discharge in the form of corona discharge. This means that the initial electrons cause an electron avalanche, which in turn produces secondary electrons, and that these secondary electrons in turn produce new electron avalanches.

The ionization processes are concentrated in the vicinity of the electrode 7, where electric field strength is at its highest. The three-dimensional load is generated and the steady corona discharge with the current $I_k$ appears in the discharge gap 1. It is noteworthy that the corona discharge takes place while the voltage Uab between electrodes lies within the interval $$Ui < Uab < Ua,$$

where
Ui=the corona ignition voltage; and
Ua=the arc breakdown voltage.

The electrodes of the dynamic discharger are then switched into a separated position by the pusher 6, and the distance between electrodes is increased at a substantially constant speed (about 1 m/s for a discharge gap of 5 m in nitrogen). An increase in the distance between electrodes causes a reduction of the interelectrode capacitance of the dynamic discharger 5, and the voltage applied to the electrodes of the dynamic discharger 5 is increased. As a result, the current of the corona discharge $I_k$ is lowered.

The intensity of lowering the current $I_k$ causes a redistribution of a three-dimensional charge near the corona-forming electrode 7. To the extent that the numbers of ions drifting along the field in the discharge gap decrease, and the processes of diffusion become more prevailing, the uniform distribution of the three-dimensional charge along the discharge gap 1 is able to take place. When the strength of the electric field between the dynamic discharger 5 and the electrodes reaches its critical value, an arc is produced across the electrodes. The electrode 7 of the main discharge gap 1 is then connected to the corresponding power supply unit 2 terminal by the arc formed between the electrodes 7 and 8. As a result, the total voltage, voltage sufficient for a complete breakdown, is supplied to the discharge gap 1 with a uniformly distributed three-dimensional load, and the breakdown of the gaseous dielectric takes place. The electrodes of the dynamic discharge device 5 are closed together, and the device is ready for the next operating cycle.

In summary, in order to perform the electrical breakdown of a gaseous dielectric, the following features are used:

1. The work of the electrical field forces made in the discharge gap 1 using the energy of the power supply unit 2; and
2. The work of mechanical forces that are made to switch the electrodes into an open state in the dynamic discharge device 5.

These two features permit the performance of gaseous insulation tests, and the diagnosis of gaseous insulation, using a simple method with a power supply unit having a relatively tow output voltage.

What is claimed is:

1. The method of electrically breaking down a gaseous dielectric in a non-uniform field created within a discharge gap, comprising the steps of supplying an initial voltage to the electrodes that form a discharge gap to create a self-maintaining discharge; and then applying to the discharge gap electrodes a voltage pulse that, with the initial voltage, causes a complete breakdown of the gaseous dielectric, application of the initial voltage to the discharge gap electrodes forming a corona discharge simultaneously with formation of a space charge near the corona-forming electrode, the space charge being evenly distributed along the discharged gap prior to formation of the voltage pulse by means of a reduction of the corona current, the reduction of the corona current and voltage pulse being effected by separating the electrodes of a dynamic discharger connected in series with the source of the initial voltage from a closed condition in which the electrodes of the dynamic discharger are connected to a separated condition in which the distance between the electrodes of the dynamic discharger is greater than a distance between the electrodes of the dynamic discharger in the closed condition until an arc is produced across the electrodes of the discharge gap.

2. A device for electrically breaking down a gaseous dielectric in a non-uniform field comprising a discharge gap for receiving the gaseous dielectric; first means for supplying an initial voltage to electrodes that form the discharge gap to create a self-maintaining discharge; second means for applying to the discharge gap electrodes as voltage pulse that, with the initial voltage, causes a complete breakdown of the gaseous dielectric, such that application of the initial voltage to the discharge gap electrodes forming a corona discharge simultaneously with formation of a space charge near the corona-forming electrode, the space charge being evenly distributed along the discharge gap prior to formation of the voltage pulse by means of a reduction of the corona current, said second means including a dynamic discharger connected in series with said first means for reducing the corona current and voltage pulse by separating the electrodes of the dynamic discharger from a closed condition in which the electrodes of the dynamic discharger are connected to a separated condition in which the distance between the electrodes of the dynamic discharger is greater than a distance between the electrodes of the dynamic discharger in the closed condition until an arc is created across the electrodes of the discharge gap.

3. A device for electrically breaking down a gaseous dielectric in a non-uniform field comprising a discharge gap for receiving the gaseous dielectric; first means for supplying an initial voltage to electrodes that form the discharge gap to create a self-maintaining discharge; second means for applying to the discharge gap electrodes as voltage pulse that, with the initial voltage, causes a complete breakdown of the gaseous dielectric, such that application of the initial voltage to the discharge gap electrodes forming a corona discharge simultaneously with formation of a space charge near the corona-forming electrode, the space charge being evenly distributed along the discharge gap prior to formation of the voltage pulse by means of a reduction of the corona current, said second means including a dynamic discharger connected in series with said first means for reducing the corona current and voltage pulse by separating the electrodes of the dynamic discharger from a closed condition in which the electrodes of the dynamic discharger are connected to a separated condition in which the distance between the electrodes of the dynamic discharger is greater than a distance between the electrodes of the dynamic discharger in the closed condition until an arc is created across the electrodes of the discharge gap; and a pusher for modifying the spacing of the dynamic discharger electrodes, the pusher normally maintaining such electrodes in contact with each other in the closed condition when the pusher is not actuated.

* * * * *